United States Patent [19]

Lampropoulos et al.

[11] Patent Number: 5,163,554
[45] Date of Patent: Nov. 17, 1992

[54] SYSTEM AND METHOD FOR PACKAGING COILS OF TUBING

[75] Inventors: Bryan R. Lampropoulos; John M. Butler, both of Salt Lake City, Utah

[73] Assignee: Merit Medical Systems, Inc., Salt Lake City, Utah

[21] Appl. No.: 818,615

[22] Filed: Jan. 10, 1992

[51] Int. Cl.$^5$ .............................................. B65D 85/04
[52] U.S. Cl. ..................... 206/363; 53/449; 53/469; 206/391; 206/438
[58] Field of Search ............... 206/363, 364, 370, 389, 206/391, 394, 438, 570; 53/430, 449, 469

[56] References Cited

U.S. PATENT DOCUMENTS

| | | | |
|---|---|---|---|
| 1,716,628 | 6/1929 | Gittleman | 206/394 |
| 2,615,112 | 10/1952 | Lagan, Jr. | 206/438 |
| 2,853,278 | 9/1958 | Hesler | 206/389 |
| 2,969,146 | 1/1961 | Metz | 206/364 |
| 4,116,338 | 9/1978 | Weichselbaum | 206/438 |
| 4,216,860 | 8/1980 | Heimann | 206/370 |
| 4,479,761 | 10/1984 | Bilstad et al. | 206/570 |
| 4,524,870 | 6/1985 | Roccaforte et al. | 206/45.33 |
| 4,850,954 | 7/1989 | Charvin | 206/438 |
| 4,925,448 | 5/1990 | Bazaral | 206/364 |

FOREIGN PATENT DOCUMENTS

| | | | |
|---|---|---|---|
| 1152354 | 2/1958 | France | 206/389 |
| 8402893 | 8/1984 | PCT Int'l Appl. | 206/389 |

Primary Examiner—Jimmy G. Foster
Attorney, Agent, or Firm—Workman, Nydegger & Jensen

[57] ABSTRACT

A system and method for packaging devices having one or more coils of delicate tubing utilizing a peel-pouch package with a backing surface and a transparent cover sealingly adhered to form an envelope wherein the device and the coils of tubing are packaged. The packaging system provides for a single releasable interconnecting coil restraint that effectively binds the coils of tubing together such that any one particular coil is restrained from moving. The restraint has an end tab facilitating the release of the restraint such that the packaged coils can be quickly and easily removed and placed into use. The restrained coils of tubing are placed within a lining sheath prior to being placed within the envelope through the envelope opening in order to further protect the packaged system by rendering the envelope puncture resistant. A heat stake is applied to the packaged envelope at an opposite end from the envelope opening to effectively reduce the volume within the envelope so as to limit the movement of the contents therein. With such a packaging system and method, the individual tubes of the coils do not bend or kink and the coils remains free from tangling and intertwining during the rough treatment normally incident to worldwide shipping and handling.

36 Claims, 7 Drawing Sheets

SYSTEM AND METHOD FOR PACKAGING COILS OF TUBING

BACKGROUND

1. Field of the Invention

The present invention relates to a system and method for packaging coils of tubing and, in particular, a system and method for packaging coils of thin-walled medical grade plastic tubing.

2. The Background History of the Prior Art

Medical grade equipment often requires special packaging to insure that the device arrives at its destination sterile and free from damage to the delicate components packaged therein. One specific problem arises in the shipping and handling of packages containing medical coils of thin-walled plastic tubing. One device in particular, the angioplasty manifold kit, contains a plurality of relatively long thin-walled plastic tubes each attached to a specific manifold outlet.

Rough handling normally incident to the worldwide shipping of packages containing manifold kits often results in damage to the delicate components contained therein. Specifically, packaged manifold kits are particularly susceptible to damage during shipment because the delicate tubing easily kinks at the point where the tubing is securely affixed to the individual manifold outlets. A sharp motion to the entire packaged kit during the shipping and handling process typically causes the tubing to bend or kink at that junction. Such a kink in one or more of the manifold tubes will impede the flow of a fluid substance therethrough. As a result of rough treatment during shipping and handling, damage by kinking or bending of any of the relatively long thin-walled lengths of coiled tubing contained in the packaged manifold kit will result in the entire manifold kit being rejected, since the entire kit comes as a sterilized unit.

Furthermore, the coils of the manifold kit must be packaged in such a manner that the coils can be easily removed from the sterile shipping package so that the angioplasty manifold kit can be quickly put into use for the patient's benefit during the medical procedure. Normal use would require that the coils be removed from the package then unwound and extended for connection to other components. If the coils are tangled, this increases the time and complexity of setting up the kit, and it is annoying to have to untangle plastic tubing that has become tangled or intertwined.

SUMMARY AND OBJECTS OF THE INVENTION

The system and method of the present invention seek to overcome specific problems inherent in the packaging of angioplasty manifold kits containing one or more relatively long coils of thin-walled medical grade plastic tubing. However, as will be appreciated, the invention as broadly conceived and described may be usefully applied to any type of coiled product which must be shipped without damage and/or tangling of the coils. In particular, the present invention is directed to a novel system and method of packaging that minimizes damage to the coils of tubes such as kinking, bending, or tangling constitutes an important advance in the art of packaging such coils.

Therefore, it is a primary object of the present invention to provide a system and method of packaging coils of tubing which simply and effectively binds the tubes such that the coils do not bend, kink, or tangle during the rough treatment normally incident to worldwide shipping and handling.

It is yet another object of the present invention to provide a system and method for packaging coils that provides for an interconnecting coil restraint that effectively binds the coils of tubing together such that the individual coils are restrained from moving and the motion of any one particular coil is limited to motion by all of the coils taken together.

It is yet a further object of the present invention to provide a system and method wherein the coils of tubing are interlocked by a single interconnecting means having shortened junctions to add increased overall rigidity to the packaged coils such that the singular motion of the contents of the packaged system is altogether further restrained.

It is still yet another object of the present system and method to provide an interconnecting coil restraint that is releasable by a single motion such that the coils of tubing can be quickly and easily freed from their interlocking restraint in order to facilitate uncoiling.

It is an additional object of the present invention to provide a system and method of packaging coils of tubing wherein a heat stake is used to reduce the volume within the envelope so as to limit the movement of the packaged contents contained therein.

It is yet another object of the present invention to provide a system and method of packaging wherein a heat stake is positioned an opposite end from the envelope opening so as not to interfere with the removal of the packaged coils from the envelope such that the ultimate use of the coils is facilitated.

It is another object of the present invention to provide a system and method of packaging that contains at least one lining sheath into which the prepared coils of tubing are positioned prior to being placed within the envelope so as to provide additional protection for the delicate medical-grade plastic tubes packaged therein by rendering the package relatively puncture resistant.

It is yet another object of the present invention to provide a system and method of packaging that is economical to assemble.

These and other objects and features of the system and method of the present invention will become more fully apparent from the following description and appended claims taken in conjunction with the accompanying drawings, or may be learned by the practice of this invention.

Briefly summarized, the system and method of the present invention provides a novel way of packaging coiled products, such as the medical-grade tubing in an angioplasty manifold kit. Such a packaging system generally comprises a peel-pouch package having a backing surface and a transparent covering surface sealingly adhered over the backing surface in order to form an envelope into which the coils are packaged. The opening in the envelope is subsequently sealed so as to enclose the packaged contents therein. In such a manner, the contents of the packaged unit can be visually inspected for damage prior to being opened for use. The novel packaging system of the present invention provides for a single releasable interconnecting coil restraint that effectively binds the coils together such that any one particular coil is restrained from moving relative to another. When stress is applied to one of the coils, the adjacent coils absorb and distribute that force.

With such a packaging system, the lateral motion of any one particular coil is limited to the uniform lateral motion of all of the coils taken together so as to effectively prevent any one tube in the series of coils from bending, kinking, or tangling, particularly at the junction where the delicate tubes connect to the manifold outlets. The interconnecting coil restraint is provided with an end tab that easily facilitates the disconnecting of the coils from the prepackaged system with a single motion.

In one embodiment, the packaging system has a lining sheath. The prepared manifold kit is positioned within the liner prior to being placed within the peel-pouch envelope. The use of a lining sheath renders the envelope puncture resistant so as to provide additional protection for the contents packaged therein.

The opening of the peel-pouch envelope is heat sealed to protect from loss of sterilization prior to the package being opened in the sterile confines of the medical facility. In one embodiment, a heat stake is further applied to the packaged envelope to reduce the volume within the envelope so as to limit the movement of the packaged contents contained therein. The heat stake is positioned at an opposite end from the envelope opening so as not to interfere with the removal of the coils of tubing from the envelope.

The novel method of packaging coils of the present invention generally comprises the steps of arranging the tubing into individual coils. The coils of tubing are then interlocked together so as to restrain the movement of the coils relative to one another. The prepared contents are next placed into a lining sheath to further render the envelope puncture resistant. The lining sheath, which contains the prepared manifold kit, is then placed into the peel-pouch envelope. A transparent cover enables the contents of the package to be visually inspected for damage prior to opening the package for use. The envelope is then heat staked in order to reduce the volume within the envelope in order to limit the movement of the contents therein. The heat stake is positioned at an opposite end from the envelope opening so as not to interfere with the removal of the coils of tubing from the envelope. The opening of the peel-pouch envelope package is sealed to enclose the coils of tubing within and the entire package and its contents are then sterilized.

With such a novel system and method for packaging, the delicate coils of tubing, as those of the angioplasty manifold kit, do not bend, kink, or tangle during the rough treatment normally incident to worldwide shipping and handling. The packaging system and method facilitates the inspection of the contents of the package prior to opening. Further, the removal of the packaged contents from the shipping package is facilitated such that the medical device can be quickly and easily placed into use.

BRIEF DESCRIPTION OF THE DRAWINGS

In order to more fully understand the manner in which the above-recited advantages and objects of the system and method of the present invention are obtained, a more particular description of the invention will be rendered by reference to specific embodiments thereof which are illustrated in the appended drawings. Understanding that these drawings depict only one or more embodiments of the invention and are therefore not to be considered limitations in the scope of the invention, the presently preferred embodiments and the presently understood best mode of the invention will be described with additional detail through use of the accompanying drawings in which.

DETAILED DESCRIPTION OF THE PREFERRED EMBODIMENTS

Reference is now made to the drawings wherein like parts are designated with like numerals throughout.

A. The system of the Present Invention

Figure 1:
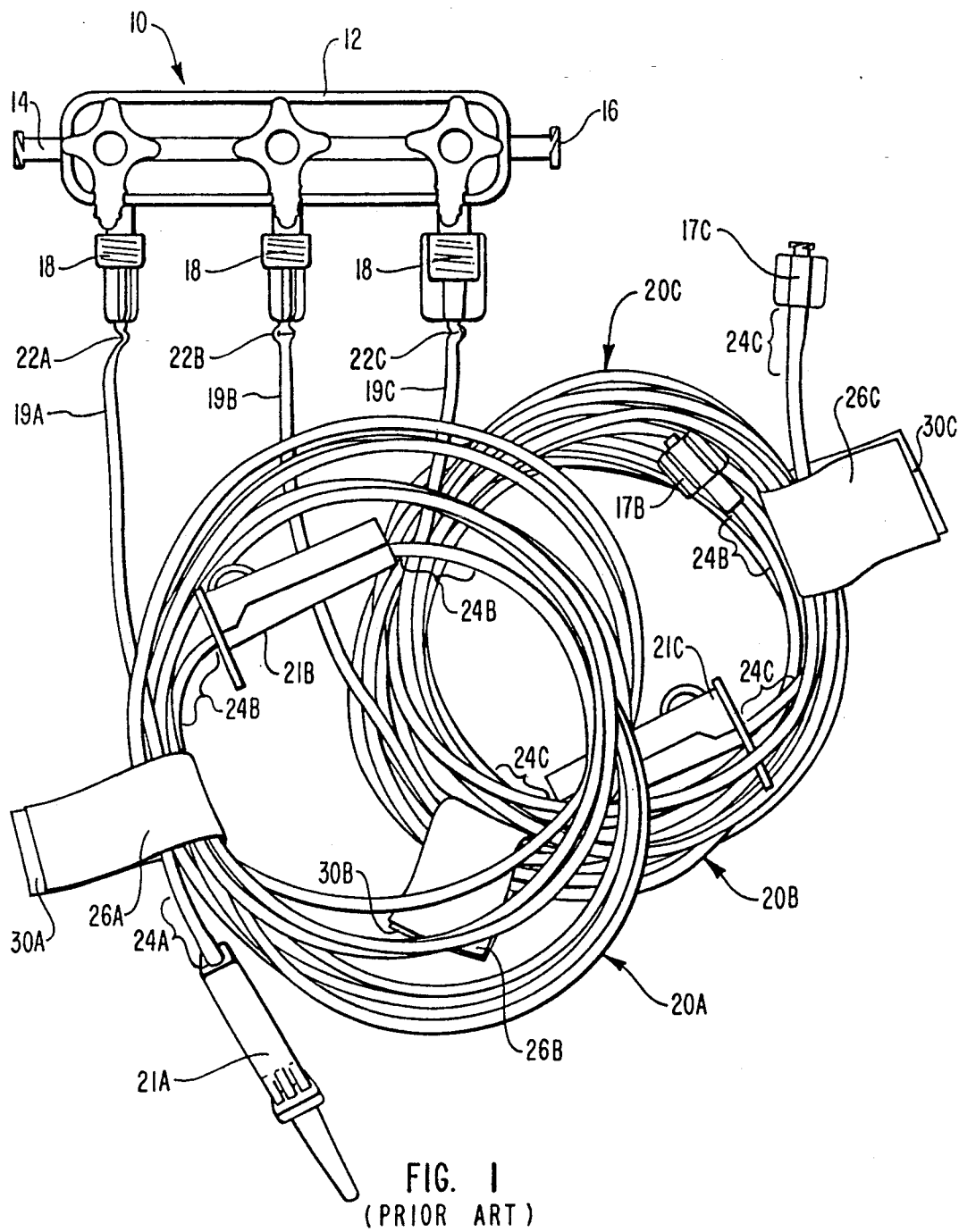
FIG. 1 is a front perspective view of a damaged angioplasty manifold kit illustrating prior art problems of kinking of the delicate tubing at the junction where the tubes connect to the manifold outlets.

In order to best understand the problems in the art which are solved by the invention, reference is now made to FIG. 1 which illustrates a damaged angioplasty manifold kit, generally designate at 10, comprising a manifold 12, fluid ports 14 and 16, and, in this embodiment, three coils of tubing, designated as 20A, 20B, and 20C. The present manifold comprises three manifold outlets, each designated at 18, to which the individual tubes, 19A, 19B, and 19C are individually and securely attached. Connected to the end of tube 19A is an irrigation attachment 21A that secures to a fluid source, such as saline or contrast media, for introduction into the patient through the manifold. Tubes 19B and 19C are connected through fluid flow regulators, at 21B and 21C, which provide the medical professional with the ability to control the flow of the fluid through the individual tubes. The ends of tubes, 19B and 19C, have tube end connectors, 17B and 17C, which enable the medical professional to connect the individual tubes to various fluid sources.

In FIG. 1, the individual coils of tubing 20A, 20B, and 20C, are individually bound by an cohesive tape, designated as 26A, 26B, and 26C, each having an end tab 30A, 30B, and 30C. Under these restraints, the individual coils are free to move within a package thereby resulting in bending and kinking, generally, at regions 22A, 22B, and 22C. Further and with respect to coil 20A of tubing 19A, movement of irrigation attachment 21A may cause tube 19A to bend and kink at region 24A. Similar and with respect to coils 20B and 20C, movement of the fluid flow regulators, 21B and 21C, and the tube end connectors, 17B and 17C, which are attached to tubes 19B and 19C, may cause the tubes to bend or kink, generally, at regions 24B and 24C. In this regard, FIG. 1 illustrates prior art problems incident to packaging coils of delicate medical-grade tubing such as the bending and kinking of the tubing due to rough handling of the packages.

Figure 2:
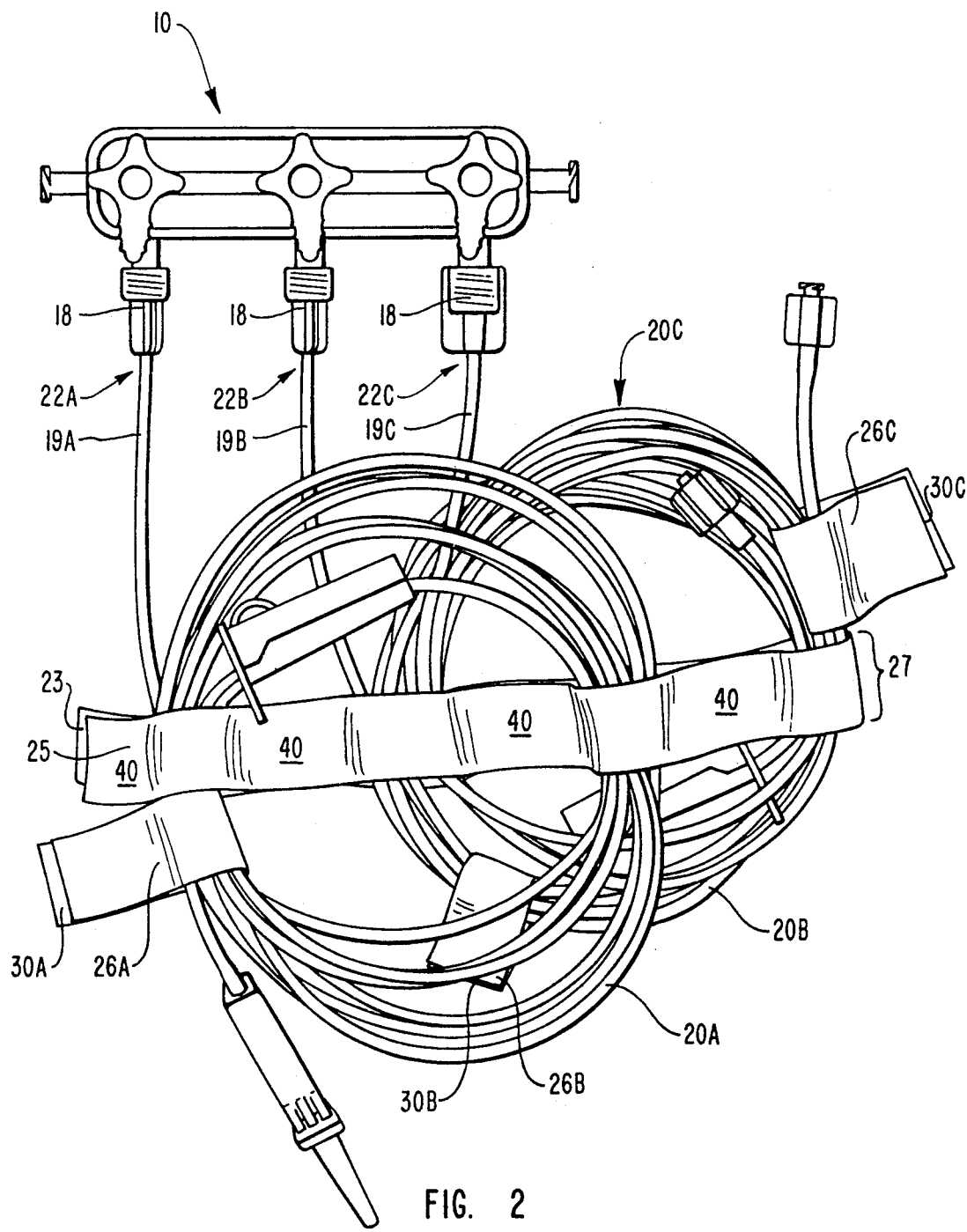
FIG. 2 is a front perspective view of the manifold kit of FIG. 1, illustrating one embodiment of the system and method of packaging of the present invention wherein the coils of tubing are bound together by a releasable interconnecting coil restraint.

FIG. 2 best illustrates one embodiment of the system and method of packaging of the present invention wherein the coils of tubing, 20A, 20B and 20C, are bound together by a single coil interconnecting means for interlocking the coils of tubing so as to restrain movement of the coils relative to one another. In the presently preferred embodiment illustrating the packaging system with an angioplasty manifold kit, the means for interlocking the coils of tubing may comprise, for example, a strip of cohesive tape 25 having a single relatively sticky side. In this embodiment, the cohesive tape 25 is folded around coils 20A, 20B, and 20C at about the midpoint 27 of the tape's length. The folding of the cohesive tape 25 onto itself creates securely held rigid junctions 40 wherein the movement of the coils of tubing is restrained. The interconnecting coil restraint 25 has end tab 23 to facilitate the release of the coil restraint 25 by a single motion of one hand such that all the coils of tubing can be quickly and easily freed in order to facilitate set up of the angioplasty manifold kit. Although, in the presently preferred embodiment the releasable coil interconnecting means for interlocking the coils of tubing together comprises a releasably cohesive tape 25, other releasable interconnecting means are contemplated by this invention, such as an adhesive tape, a Velcro strip, a plastic interconnector, or the like, and therefore are to be considered within the scope of the present invention.

Figure 3:
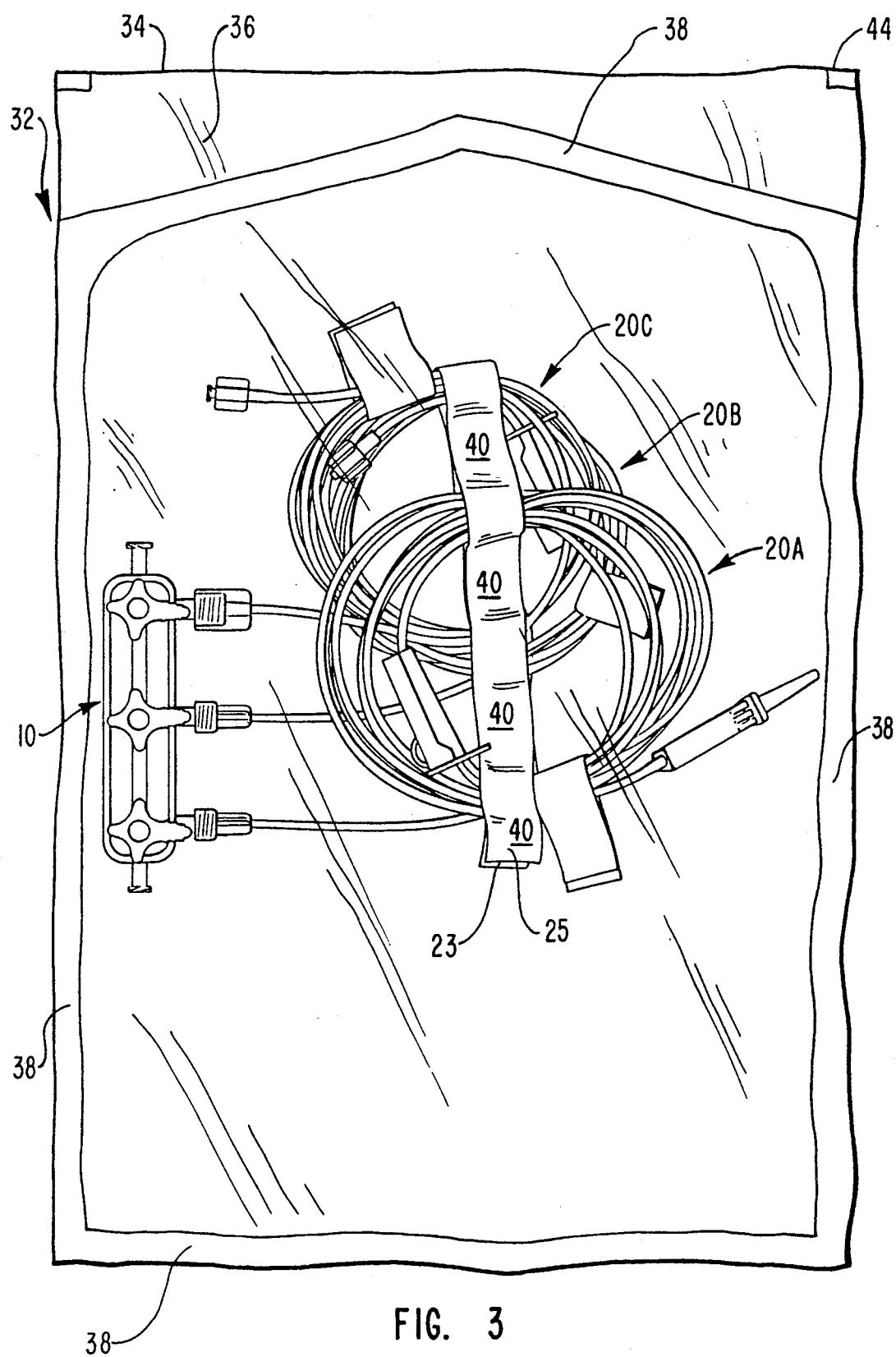
FIG. 3 is a front perspective view of the prepared manifold kit of FIG. 2, illustrating the embodiment wherein the coils of tubing are placed, as a unit, within a peal-pouch envelope having a transparent covering surface that is sealed to a backing surface paper.

The embodiment of FIG. 2 is illustrated in FIG. 3 wherein the coils of tubing 20A, 20B, and 20C are placed, as a unit, within a peel-pouch envelope, designated at 32, which is well-known in the packaging arts. In this embodiment, the peel-pouch envelope 32 has a backing surface 34 generally comprising a gas-permeable material that can undergo ethyleneoxide sterilization while remaining resistant to tearing and puncturing. A covering surface 36 is sealingly adhered, in the region designated as 38, to the backing surface 34 so as to enclose and protect the packaged coils. The covering surface 36 comprises a material that is transparent in order to enable the contents inside the envelope to be visibly inspected for damage prior to opening. Backing and cover surfaces 34 and 36 may also be formed of materials that can undergo E-beam and radiation sterilization while remaining resistant to tearing and puncturing. FIG. 3 illustrates one embodiment of the present system as is used for packaging angioplasty manifold kits having individual coils of tubing. Such a packaged system simply and effectively binds the tubes such that the coils do not bend or kink and that the coils remain free from tangling and intertwining during the rough treatment normally incident to worldwide shipping and handling.

Figure 4:
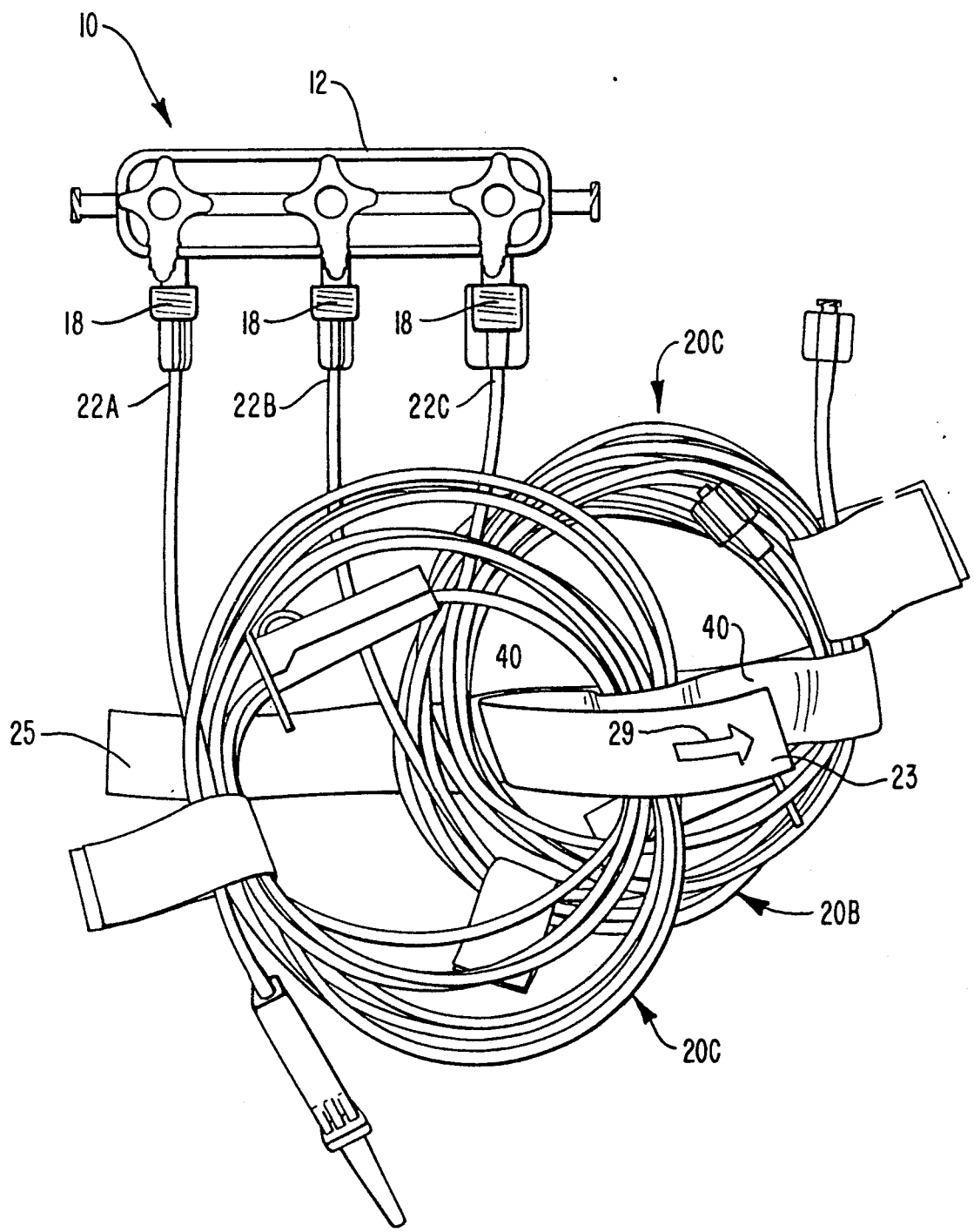
FIG. 4 is a front perspective view of the embodiment of FIG. 2, illustrating how quickly and easily the coil interconnecting means for interlocking the coils of tubing can be released.

With reference now to FIG. 4, the interlocking restraint 25, of the packaged angioplasty manifold kit of the embodiment illustrated in FIG. 2, can easily be removed. The cohesive tape 25, for interlocking the coils of tubing 20A, 20B, and 20C, has a convenient end tab 23 which is releasable by simply pulling the tape apart, as is schematically illustrated by the directional arrow 29 placed on the inner side of cohesive tape 25. It is preferable that the cohesive tape 25 be strong enough to form junctions 40, adding to the overall rigidity of the packaged system so as to effectively bind the series of coils together in order to prevent bending and kinking, while enabling the medical professional to quickly remove the restraint with a single easy pulling motion of one hand.

Figure 5:
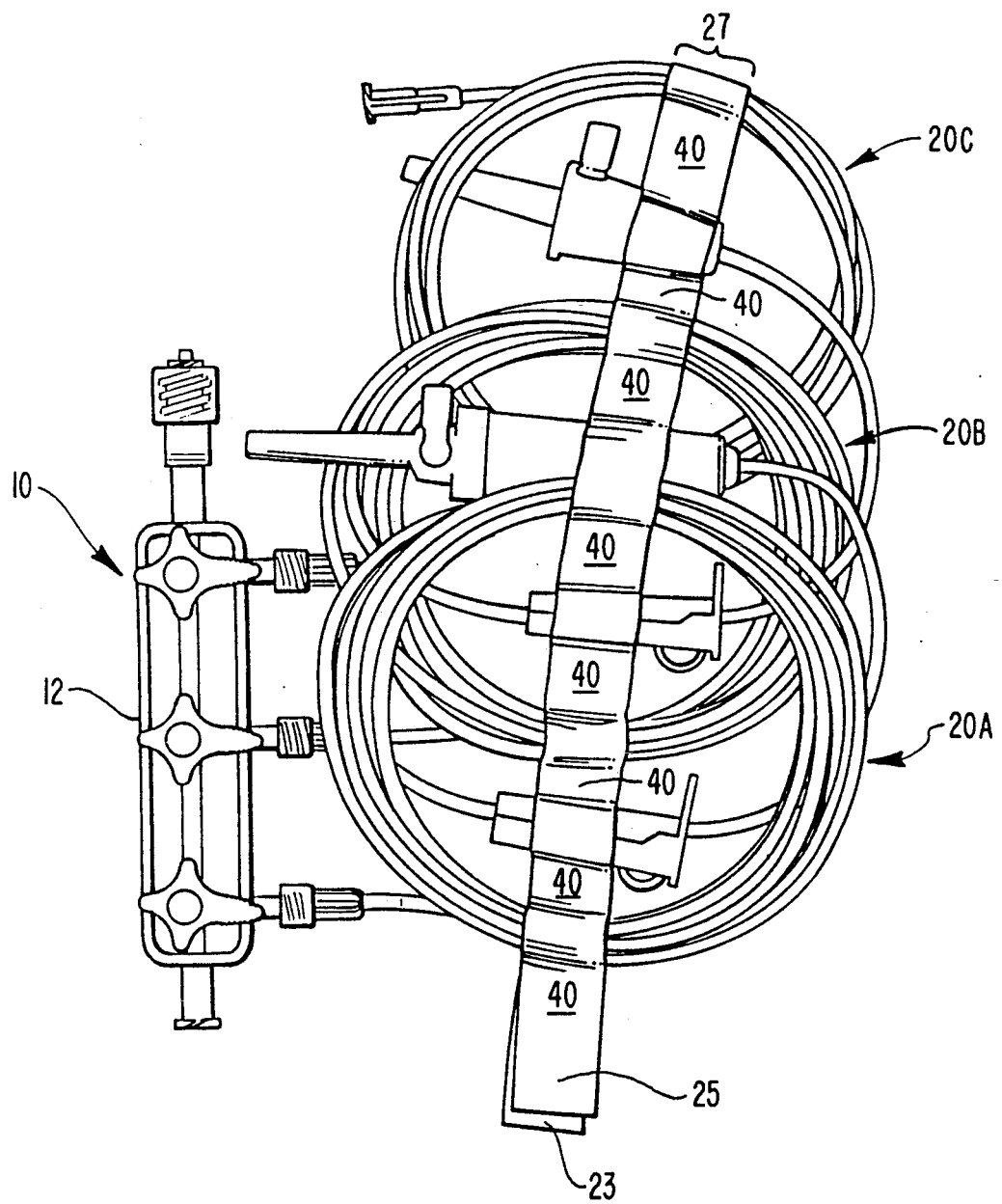
FIG. 5 is a front perspective view of another embodiment of the system and method of packaging of the present invention wherein the coils of tubing are interlocked by a single interconnecting means having shortened junctions to add increased overall rigidity to the system of packaged coils of tubing.

In another embodiment within the scope of the present invention illustrated by FIG. 5, the coils of tubing 20A, 20B, and 20C, are interlocked by a single interconnecting means similar to the interconnecting means of the embodiment of FIGS. 1 through 4. In this embodiment, the means for interlocking the coils of tubing also comprises, by way of example, a strip of cohesive tape 25 having a single relatively sticky side which is folded around coils 20A, 20B, and 20C at about the midpoint 27 of the tape's length. The folding of the cohesive tape 25 onto itself creates rigid junctions 40. In this embodiment, the cohesive tape is secured around the components, such as the flow regulators and the irrigation attachments connected around and to individual tubes 19A, 19B, and 19C. In such a manner, the cohesive tape creates shortened junctions 40 to add increased overall rigidity to the system of packaged coils of tubing, thus, the movement of the packaged coils of tubing, 20A, 20B, and 20C, is restrained because the cohesive tape 25 encompasses all the contents of the packaged unit. The cohesive tape 25 of this embodiment also has an end flap 23 to allow the medical professional to release the cohesive restraint by the single motion of one hand.

It is to be understood and appreciated that each of the stated interconnecting means with the associated end flap can be designed in a variety of different ways while still performing the same functions as described by way of illustration with respect to such means, and such variations are therefore intended to be within the scope of the invention as broadly described and claimed herein.

Figure 6:
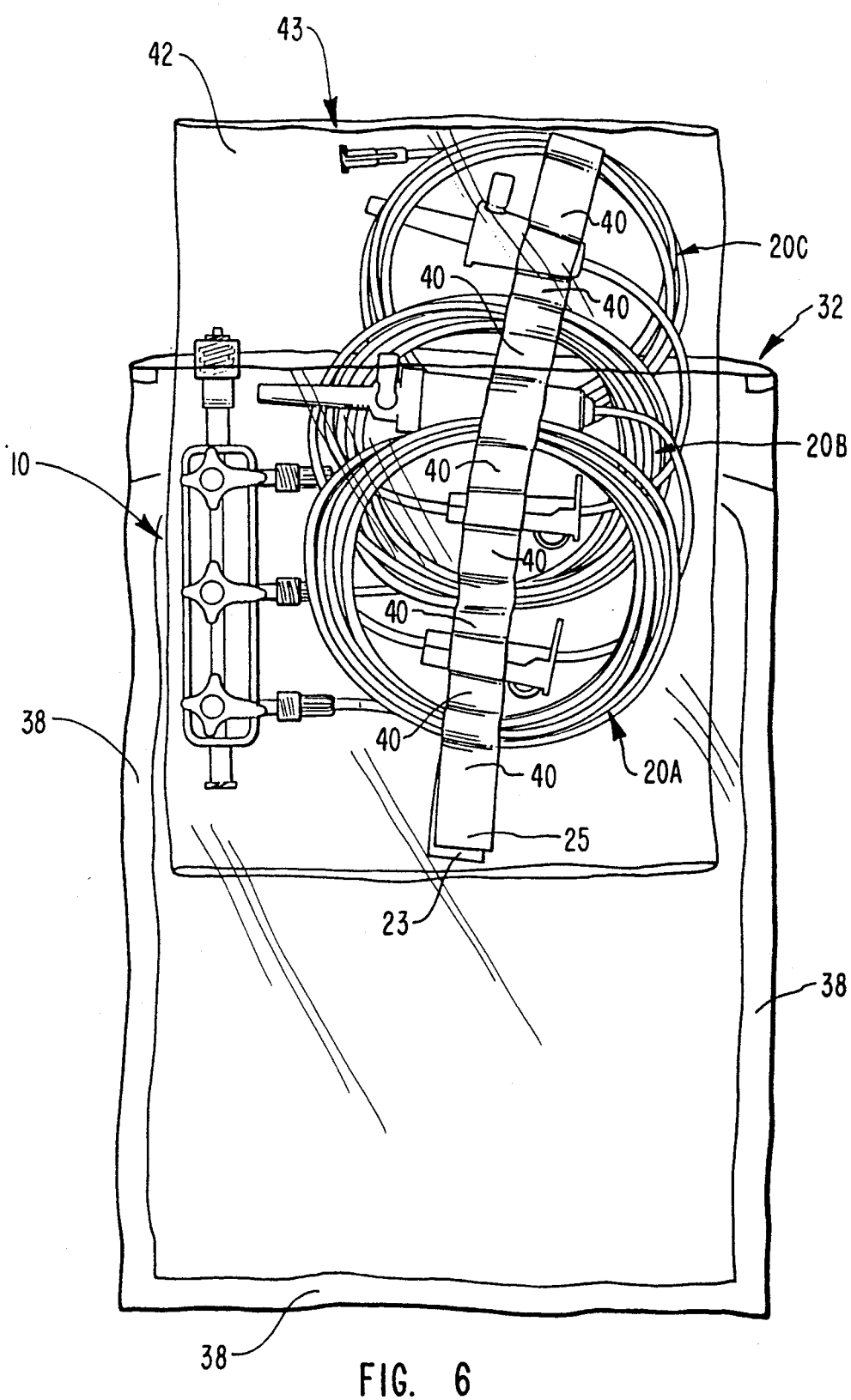
FIG. 6 is a front perspective view of the embodiment of FIG. 5, further illustrating the use of a lining sheath into which the prepared manifold kit is positioned prior to placing the entire lining into the peel-pouch envelope.

Reference is now made to FIG. 6 further illustrating one embodiment encompassing the use of a lining sheath 40. In the illustrated embodiment, the lining sheath 42 is folded onto itself thereby creating opening 43 into which the prepared coils of tubing 20A, 20B, and 20C, of the manifold kit 10 are put prior to being placed into the peel-pouch envelope 32. The lining sheath is preferably of a resilient plastic material of a type commonly found in the arts sufficient to render the peel-pouch package relatively puncture resistant. It is to be understood that the present invention contemplates the use of a lining sheath in only one of the preferred embodiments to further protect the contents of the package from damage. Other forms of lining and liners for the further protection of the packaged contents, such as those made of cloth or of styrofoam construction, are contemplated and therefore to be considered within the scope of this invention as illustrated by way of the embodiment of FIG. 6.

Figure 7:
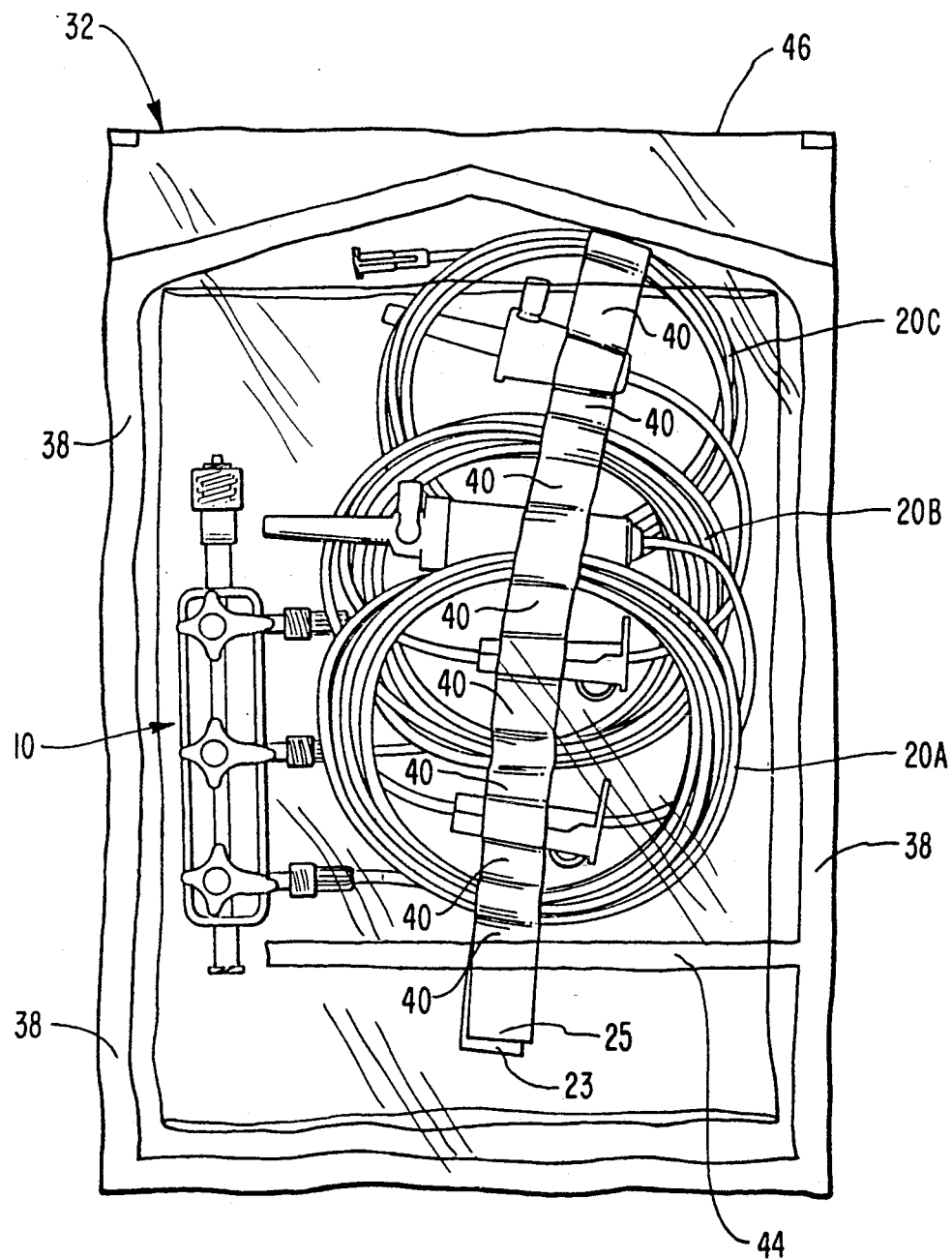
FIG. 7 is a front perspective view of the embodiment of FIGS. 5 and 6, further illustrating the use of a heat seal to seal the opening of the peel-pouch and the use of a heat stake positioned at an opposite end from the envelope opening in order to reduce the volume within the envelope so as to limit the movement of the coils of tubing contained therein.

FIG. 7, a perspective view of the embodiments of FIGS. 5 and 6, shows the preferred completed system of packaging of the present invention. A heat seal 38 closes the opening of the peel-pouch envelope 32 to effectively seal the contents within the envelope. A heat stake at 44 is used to reduce the volume within the envelope 32 so as to limit the movement of the contents therein. The heat stake 44 is positioned at an opposite end from the opening end 46 of the peel-pouch envelope 32 so as not to interfere with the removal of the packaged contents such that their use is facilitated.

The Method of the Present Invention

In one presently preferred embodiment as illustrated in FIG. 2, the method of the present invention comprises the steps of arranging the tubes 19A, 19B, and 19C into individual coils 20A, 20B, and 20C. With reference being made next to FIG. 5, the individual coils of tubing 20A, 20B, and 20C, are then interlocked and interconnected together by an cohesive tape 25 so as to restrain the movement of the coils and to secure the attachments to the individual tubes such that the relative motion of each of these packaged components is restricted. The cohesive tape 25 is folded onto itself around the components of the packaged system so as to create rigid junctions 40 which add to the overall rigidity of the system such that the singular motion of any of the contents within the package further restrained. With reference now to FIG. 6, in this embodiment the prepared manifold kit 10 is placed into a lining sheath 42 to protect the contents contained therein. The lining sheath 42 containing the manifold kit 10 is then placed into a peel-pouch envelope 32 to further render the envelope puncture resistant. The peel-pouch envelope has a transparent cover 36 which enables the contents of the package to be visually inspected for damage prior to opening the package for use. The envelope 32 is then heat staked, shown at 44 in FIG. 7, in order to reduce the volume within the envelope so as to limit the movement of the packaged contents. The heat stake 44 is positioned at an opposite end from the envelope opening 46 so as not to interfere with the removal of the packaged contents from the envelope. The opening 46 of the peel-pouch envelope 32 is sealed at 38 by a heat sealing process commonly found in the packaging arts in order to enclose the manifold kit 10 therein. Prior to shipping, the entire packaged is sterilized in order to render the contents thereof innocuous.

In summary, with such a novel system and method for packaging coils, such as those contained in the angioplasty manifold kit, the individual tubes of the coils do not bend or kink, particularly at the region where the tubes are attached to the manifold outlets, and the packaging system simply and effectively binds the coils such that the coils remains free from tangling and intertwining during the rough handling normally incident to worldwide shipping and handling. Further, the packaging system and method facilitates the removal of the series of coils from the shipping package such that the medical device can be quickly and easily placed into use for the patient's benefit.

The system and method of the present invention may be embodied in other specific forms without departing from the spirit of this invention or its essential characteristics. The described embodiments are to be considered, in all respects, as illustrative and not restrictive. The scope of the invention is, therefore, indicated by the appended claims rather than by the foregoing description. All changes which come within the meaning and range of equivalency of the foregoing claims are to be embraced within their scope.

What is claimed and desired to be secured by United States Letters Patent is:

1. A system for packaging a plurality of separate tubes into a plurality of non-concentric coils of tubing, said system comprising:
   a backing surface;
   a covering surface over said backing surface to form an envelope into which said coils are packaged; and
   a releasable coil interconnecting means for interlocking the plurality of non-concentric coils of separate tubes together so as to restrain movement of the coils relative to one another.

2. A system for packaging coils of tubing as defined in claim 1, wherein said backing and covering surfaces are each comprised of a flat sheet which together form said envelope, and further comprising at least one liner placed within said envelope and around said coils so as to make the envelope puncture resistant.

3. A system for packaging coils of tubing as defined in claim 1, wherein said envelope comprises an opening at one end thereof and further comprising a heat stake positioned at an opposite end from the envelope opening in order to reduce the volume within said envelope so as to limit the movement of the coils of tubing contained therein.

4. A system as defined in claim 3, wherein said opening in said envelope between said backing surface and said covering surface is sealed so as to enclose the coils of tubing therein.

5. A system as defined in claim 1, wherein said releasable coil interconnecting means for interlocking the coils of tubing together comprises a releasably cohesive tape.

6. A system as defined in claim 1, wherein said covering surface comprises a material that is transparent in order to enable the coils of tubing inside the envelope to be visibly inspected for damage prior to opening.

7. A system as defined in claim 1, wherein said covering surface is sealingly adhered to said backing surface so as to enclose and protect the coils of tubing within said envelope.

8. A system as defined in claim 1, wherein said backing and covering surfaces each comprise a material that can undergo E-beam and radiation sterilization while remaining resistant to tearing and puncturing.

9. A system as defined in claim 1, wherein said backing surface comprises a gas-permeable material that can undergo ethylene-oxide sterilization while remaining resistant to tearing and puncturing.

10. A system as defined in claim 1, wherein said releasable coil interconnecting means for interlocking the coils of tubing interconnects around all of the components contained in said envelope.

11. A system for packaging a plurality of separate tubes into a plurality of non-concentric coils of tubing, said system comprising:
    a backing surface;
    a covering surface over said backing surface to form an envelope into which said coils are packages; and
    a releasable coil interconnecting means for interlocking the plurality of non-concentric coils of separate tubes together so as to restrain movement of the coils relative to one another; and
    at least one liner placed within said envelope and around said coils.

12. A system for packaging coils of tubing as defined in claim 11, wherein said releasable coil interconnecting means for interlocking the coils of tubing together comprises a releasably cohesive tape.

13. A system for packaging coils of tubing as defined in claim 12, wherein said envelope comprises an opening at one end thereof and further comprising a heat stake positioned at an opposite end from the envelope opening in order to reduce the volume within said envelope so as to limit the movement of the coils of tubing contained therein.

14. A system as defined in claim 13, wherein said opening in said envelope between said backing surface and said covering surface is releasably sealed so as to enclose the coils of tubing therein.

15. A system for packaging coils of tubing as defined in claim 11, wherein said liner comprises a material that renders the envelope puncture resistant.

16. A system as defined in claim 11, wherein said covering surface and said liner comprises a material that is transparent in order to enable the coils of tubing inside the envelope to be visibly inspected for damage prior to opening.

17. A system as defined in claim 16, wherein said covering surface is sealingly adhered to said backing surface so as to enclose and protect the coils of tubing within said envelope.

18. A system as defined in claim 16, wherein said backing and covering surfaces each comprise a material that can undergo E-beam and radiation sterilization while remaining resistant to tearing and puncturing.

19. A system as defined in claim 16, wherein said backing surface comprises a gas-permeable material that can undergo ethylene-oxide sterilization while remaining resistant to tearing and puncturing.

20. A system as defined in claim 11, wherein said releasable coil interconnecting means for interlocking the coils of tubing interconnects around all of the components contained in said envelope.

21. A system for packaging a plurality of separate tubes into a plurality of non-concentric coils of tubing, said system comprising:
 a backing surface;
 a covering surface over said backing surface to form an envelope into which said coils are packaged; and
 a releasable coil interconnecting means for interlocking the plurality of non-concentric coils of separate tubes together so as to restrain movement of the coils relative to one another; and
 a heat stake means for reducing the volume within said envelope so as to limit the movement of the coils of tubing contained therein.

22. A system for packaging coils of tubing as defined in claim 21, wherein said releasable coil interconnecting means for interlocking the coils of tubing together comprises a releasably cohesive tape.

23. A system for packaging coils of tubing as defined in claim 21, further comprising at least one liner placed within said envelope and around said coils so as to make the envelope puncture resistant.

24. A system for packaging coils of tubing as defined in claim 21, wherein said envelope comprises an opening at one end thereof and wherein said heat stake is positioned at an opposite end from the envelope opening so as not to interfere with the removal of the coils of tubing from the envelope.

25. A system as defined in claim 24, wherein said opening in said envelope between said backing surface and said covering surface is releasably sealed so as to enclose the coils of tubing therein.

26. A system as defined in claim 21, wherein said covering surface comprises a material that is transparent in order to enable the coils of tubing inside the envelope to be visibly inspected for damage prior to opening.

27. A system as defined in claim 26, wherein said covering surface is sealingly adhered to said backing surface so as to enclose and protect the coils of tubing within said envelope.

28. A system as defined in claim 27, wherein said backing and covering surfaces each comprise a material that can undergo E-beam and radiation sterilization while remaining resistant to tearing and puncturing.

29. A system as defined in claim 26, wherein said backing surface comprises a gas-permeable material that can undergo ethylene-oxide sterilization while remaining resistant to tearing and puncturing.

30. A system as defined in claim 21, wherein said releasable coil interconnecting means for interlocking the coils of tubing interconnects around all of the components contained in said envelope.

31. A system for packaging coils of medical tubing, said system Comprising:
 a backing surface;
 a covering surface over said backing surface and sealingly adhered to said backing surface to form an envelope into which said coils are packaged, said envelope comprising at one end a sealable opening between said backing surface and said covering surface;
 at least one liner placed within said envelope and around said coils so as to make the envelope puncture resistant;
 a releasable cohesive tape interconnecting and interlocking the coils of tubing together so as to restrain movement of the coils relative to one another; and
 a heat stake to reduce the volume within said envelope so as to limit the movement of the coils of tubing contained therein, said heat stake positioned at an opposite end from the envelope opening so as not to interfere with the removal of the coils of tubing from the envelope opening.

32. A method for packaging coils of medical tubing comprising the steps of:
 arranging the tubing into individual coils;
 interlocking the coils of tubing together so as to restrain movement of the coils relative to one another;
 placing the interlocked coils of tubing into a lining sheath;
 placing the interlocked coils of tubing and lining into an envelope, having a backing surface and a covering surface, through an opening between the surfaces; and
 sealing the opening between said covering surface and said backing surface so as to enclose the coils of tubing within said envelope.

33. A method for packaging coils of tubing as defined in claim 32, further comprising the step of heat staking the envelope in order to reduce the volume within said envelope to limit the movement of the interlocked coils contained therein, said heat stake positioned at an opposite end from the envelope opening so as not to interfere with the removal of the coils of tubing from the envelope.

34. A method for packaging coils of tubing comprising the steps of:

arranging the tubing into individual coils;

interlocking the coils of tubing together so as to restrain movement of the coils relative to one another;

placing the interlocked coils of tubing into an envelope, having a backing surface and a covering surface, through an opening between the surfaces;

heat staking the envelope in order to reduce the volume within said envelope to limit the movement of the interlocked coils contained therein, said heat stake positioned at an opposite end from the envelope opening so as not to interfere with the removal of the coils of tubing from the envelope; and sealing the opening between said covering surface and said backing surface so as to enclose the coils of tubing within said envelope.

35. A method for packaging coils of tubing as defined in claim 34, further comprising the step of placing the interlocked coils of tubing into a lining sheath prior to placing the interlocked coils into the envelope.

36. A method for packaging coils of medical tubing comprising the steps of:

arranging the tubing into the individual coils;

interlocking the coils of tubing together so as to restrain movement of the coils relative to one another;

placing the interlocked coils of tubing into a lining sheath;

placing the interlocked coils of tubing and lining into an envelope, having a backing surface and a covering surface, through an opening between the surfaces;

heat staking the envelope in order to reduce the volume within said envelope to limit the movement of the interlocked coils contained therein, said heat stake positioned at an opposite end from the envelope opening so as not to interfere with the removal of the coils of tubing from the envelope;

sealing the opening between said covering surface and said backing surface so as to enclose the coils of tubing within said envelope; and sterilizing the sealed envelope and its contents.

* * * * *

UNITED STATES PATENT AND TRADEMARK OFFICE
CERTIFICATE OF CORRECTION

PATENT NO. : 5,163,554

DATED : November 17, 1992

INVENTOR(S) : Bryan R. Lampropoulos, et al

It is certified that error appears in the above-identified patent and that said Letters Patent is hereby corrected as shown below:

```
Abstract, line 23, "remains" should be --remain--
Column 2, line 30, after "positioned" insert --at--
Column 4, line 45, "system" should be --System--
Column 4, line 49, "designate" should be --designated--
Column 4, line 67, "an" should be --a--
Column 7, line 10, before "The" insert --B.--
Column 7, line 44, "packaged" should be --package--
Column 10, line 25, "Comprising" should be --comprising--
```

Signed and Sealed this

Second Day of November, 1993

Attest:

BRUCE LEHMAN

*Attesting Officer*  *Commissioner of Patents and Trademarks*